United States Patent
Podrebarac et al.

(10) Patent No.: US 6,242,661 B1
(45) Date of Patent: Jun. 5, 2001

(54) PROCESS FOR THE SEPARATION OF ISOBUTENE FROM NORMAL BUTENES

(75) Inventors: Gary G. Podrebarac, Nassau Bay; John R. Adams, Houston, both of TX (US)

(73) Assignee: Catalytic Distillation Technologies, Pasadena, TX (US)

( * ) Notice: Subject to any disclaimer, the term of this patent is extended or adjusted under 35 U.S.C. 154(b) by 0 days.

(21) Appl. No.: 09/354,978

(22) Filed: Jul. 16, 1999

(51) Int. Cl.[7] .................................................. C07C 5/25
(52) U.S. Cl. ..................... 585/664; 585/670; 208/138; 208/141; 203/29
(58) Field of Search ..................... 585/253, 259, 585/664, 809, 670; 208/141, 138; 203/DIG. 6, 29

(56) References Cited

U.S. PATENT DOCUMENTS

| | | | |
|---|---|---|---|
| 2,403,672 | * 7/1946 | Matuszak | 260/683.2 |
| 4,242,530 | * 12/1980 | Smith, Jr. | 585/510 |
| 4,447,668 | 5/1984 | Smith, Jr. et al. . | |
| 4,482,775 | 11/1984 | Smith, Jr. . | |
| 4,551,567 | 11/1985 | Smith, Jr. . | |
| 4,691,073 | 9/1987 | Michaelson . | |
| 4,731,229 | 3/1988 | Sperandio . | |
| 5,073,236 | 12/1991 | Gelbein et al. . | |
| 5,087,780 | 2/1992 | Arganbright . | |
| 5,266,546 | 11/1993 | Hearn . | |
| 5,595,634 | 1/1997 | Hearn et al. . | |
| 5,730,843 | 3/1998 | Groten et al. . | |
| 5,888,355 | * 3/1999 | Mikitenko et al. | 203/DIG. 6 |
| 5,969,203 | * 10/1999 | Dorbon et al. | 585/324 |
| 6,005,150 | * 12/1999 | Vora | 585/324 |

* cited by examiner

*Primary Examiner*—Bekir L. Yildirim
(74) *Attorney, Agent, or Firm*—Kenneth H. Johnson

(57) ABSTRACT

A process for the separation of isobutene, otherwise inseparable from butene-1 by fractionation, in high purity from butenes contained in a mixed hydrocarbon stream containing butene-1, butene-2 and small amounts of butadiene in which the mixed hydrocarbon stream is fed to distillation column reactor containing an alumina supported palladium oxide catalyst. The column is operated to tend to exclude butene-2 from contact with the catalyst and to maintain butene-1 in contact with the catalyst to isomerize the butene-1 to butene-2. As butene-2 is produced it is distilled away from the catalyst, upsetting the equilibrium and allowing for a greater than equilibrium amount of butene-2. The isobutene and isobutane are concurrently separated from the butene-2. Additionally, any butadiene in the feed is hydrogenated to butenes. The bottoms is rich in butene-2.

14 Claims, 1 Drawing Sheet

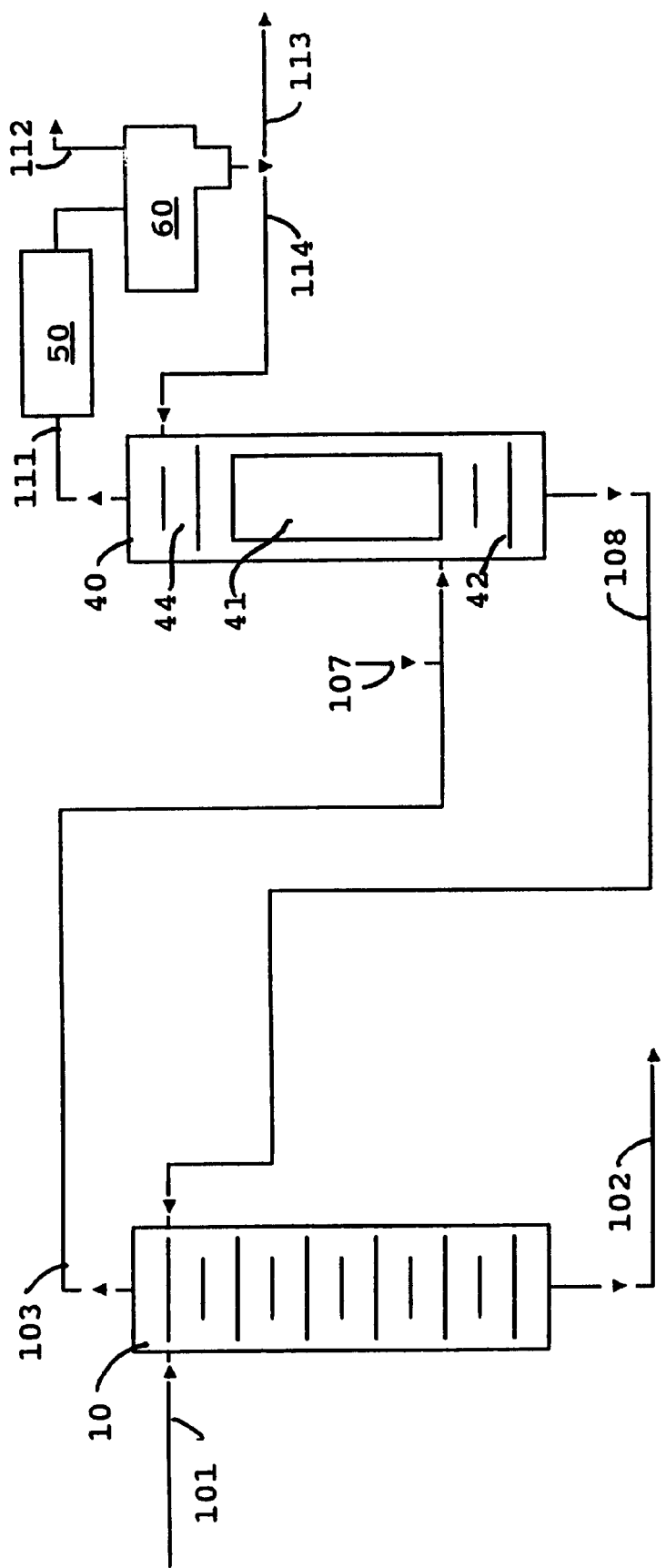

PROCESS FOR THE SEPARATION OF ISOBUTENE FROM NORMAL BUTENES

BACKGROUND OF THE INVENTION

1. Field of the Invention

The present invention relates to a process for the separation of isobutene from normal butenes in a mixed $C_4$ refinery stream. More particularly, the invention relates to a process where the butene-1 in the stream is isomerized to butene-2 to facilitate the separation. More particularly, the invention relates to a process wherein the isomerization of butene-1 to butene-2 and the separation of the butene-2 from the isobutene takes place in a distillation column reactor.

2. Related Information

Isobutene in some utilizations such as oligomerization or polymerization must have a high degree of purity, that is, be substantially free of other $C_4$ isomers such as butene-1 or butene-2. The separation of commercial quantities of isobutene from butene-1 by fractional distillation is quite difficult because of their close boiling points (isobutene −6.9° C.; butene-1 −6.3° C.). On the other hand butene-2 which boils at 1.0° C. (trans butene-2) and 3.7° C. (cis butene-2) is much more easily separated by distillation.

In order to achieve the requisite purities, processes have been developed such as etherification which reacts isobutene then recovers the ethers, followed by disassociation of the ethers to produce isobutene and alcohol which are easily separated by distillation (see U.S. Pat. Nos. 4,447,668; 4,482,775; 4,551,567 and 4,691,073).

It has been known for some time that olefins can be isomerized under mild conditions using a catalyst of palladium oxide supported on alumina in the presence of hydrogen. The actual active catalyst is probably palladium hydride which is produced during operation.

As commercialized, hydroisomerization is a process used to upgrade $C_4$ streams, usually from fluid catalytic cracking units. In the fixed bed process as practiced by some, butadiene contaminating the feed is hydrogenated to butenes, and the butenes are isomerized to the equilibrium mixture which is predominately butene-2. The advantage of that process is to remove butadiene which causes the loss of acid used in the alkylation process and improvement of the alkylate octane number in HF alkylation by using mostly butene-2 in the feed rather than butene-1.

Palladium catalysts are known and used for the butene-1 to butene-2 isomerization. As a matter of fact, one source, IFP, does not recommend palladium because of its activity for use in streams where butene-1 is to be recovered.

According to the literature, isomerization occurs only after hydrogenation of the butadiene. In the fixed bed processes a three to four percent relative loss of butene occurs due to hydrogenation as the isomerization is pushed toward equilibrium.

The use of catalytic distillation processes is known in the art. See for example the series of patents assigned to Catalytic Distillation Technologies including U.S. Pat. Nos. 4,215,011; 4,232,177; 4,242,530; 4,302,356; 4,307,254; 4,336,407; 4,439,350; 4,443,559; 4,482,775; 4,504,687; 4,510,336 and 4,536,373. Catalytic distillation has been used in the isomerization of $C_4$ alkenes as noted in U.S. Pat. No. 4,482,775 listed above. However, such a process used an acidic cationic exchange resin catalyst to produce iso and normal butenes. Arganbright in U.S. Pat. No. 5,087,780 discloses a process for the isomerization of butene-2 to increase production of butene-1 in a distillation column reactor using a palladium catalyst supported on alumina.

An advantage of the present invention is the separation of isobutene from normal butene in a high degree of purity. Another advantage sought to be achieved is relatively higher production levels of butene-2 which can be more readily separated from isobutene. Another benefit would be to convert butadiene to butenes.

SUMMARY OF THE INVENTION

Briefly, the present invention is a process for separating normal butenes from isobutene by the isomerization of butene-1 to butene-2 in the presence of a particulate supported PdO catalyst prepared as a distillation packing, preferably in the presence of a effectuating amount of hydrogen, and the concurrent distillation of the isomerization product to recover isobutene as a light product and butene-2 as bottoms.

In light of the above a catalytic distillation process is provided which takes a mixed $C_4$ stream containing saturated $C_4$'s, butadiene, n-butenes and isobutene and converts the butadiene to butenes and isomerizes the butene-1 to butene-2 which has a boiling point significantly different from isobutene to allow for separation. Most (>95%) of the butene-1 is isomerized to butene-2 which is withdrawn as bottoms. The feedstream, containing the mixed $C_4$'s is fed to the distillation column reactor containing a supported palladium oxide catalyst along with sufficient hydrogen to provide for the hydrogenation of the butadiene. In the distillation column reactor the butadiene is converted to butenes and butene-1 is isomerized to butene-2 which is concentrated in the bottoms. Isobutene and isobutane are withdrawn from the distillation column reactor as overheads.

Since the butene-2 is removed from the reaction zone, the isomerization is driven away from equilibrium and more butene-2 is produced than is obtained in an equilibrium reactor (fixed bed flow through). Isobutane is also concentrated by distillation in the overheads along with the isobutene while the butene-2 is removed from the distillation reactor as bottoms.

As used herein the term "distillation column reactor" means a distillation column which also contains catalyst such that reaction and distillation are going on concurrently in the column. In a preferred embodiment the catalyst is prepared as a distillation structure and serves as both the catalyst and distillation structure.

The isobutene recovered as overheads is substantially free of n-butenes, i.e., <0.05 wt %.

BRIEF DESCRIPTION OF THE DRAWING

The FIGURE is a schematic flow diagram of a preferred embodiment of the present invention.

DETAILED DESCRIPTION OF THE PREFERRED EMBODIMENTS

A typical mixed $C_4$ stream to be separated contains the following composition with their corresponding boiling points.

|  | BP ° C.* | wt % |
|---|---|---|
| isobutane | −12.0 | 9.8 |
| isobutene | −6.9 | 36.5 |

-continued

|  | BP ° C.* | wt % |
|---|---|---|
| butene-1 | −6.3 | 3.5 |
| n-butane | −0.5 | 26.3 |
| trans butene-2 | 1.0 | 16.9 |
| cis butene-2 | 3.7 | 7.0 |

*CHEMICAL PROPERTIES HANDBOOK, Carl L. Yaws, McGraw-Hill, 1999

The closeness of the boiling points of butene-1 and isobutene make the separation of butene-1 from isobutene difficult by distillation. However, the boiling point of butene-2 is almost 8 degrees higher for the trans isomer and more than 10 degrees for the cis isomer. Therefore, as the butene-1 is isomerized to butene-2 the normal butenes (as butene-2) can be more readily separated from the isobutene and isobutane.

The isomerization reaction is reversible as may be noted by references to "equilibrium" concentration in fixed bed reactors for a given residence time. In a catalytic distillation, i.e., the catalyst serves as a distillation component, the equilibrium is constantly disturbed, thus the removal of butene-2 as a bottoms product constantly drives the reaction to increase production of butene-2.

Broadly stated, the catalytic material is a component of a distillation system functioning as both a catalyst and distillation packing, i.e., a packing for a distillation column having both a distillation function and a catalytic function. The reaction system can be described as heterogenous since the catalyst remains a distinct entity.

The catalytic material employed in the isomerization process is preferably in a form to serve as distillation packing in such conventional distillation packing shapes as Raschig rings, Pall rings, saddles or the like and as such other structures as, for example, balls, irregular, sheets, tubes, spirals, packed in bags or other structures (such as those described in U.S. Pat. Nos. 4,242,530; 4,443,559; 5,189,001; 5,348,710 and 5,431,890), plated on grills or screens, or reticulated polymer foams (the cellular structure of the foams must be sufficiently large so as to not cause high pressure drops through the column, or otherwise arranged such as in chunks or concentration tubes to allow vapor flow). Similarly the catalyst may be employed as palladium oxide supported on ⅛" alumina extrudates, either in bags or loosely packed in the column. Preferably, the catalyst is contained in a structure as disclosed in U.S. Pat. Nos. 5,730,843; 5,266,546; 4,731,229 and 5,073,236; which are incorporated by reference.

The present invention preferably carries out the method in a catalyst packed column which can be appreciated to contain a vapor phase and some liquid phase as in any distillation. The success of the catalytic distillation approach lies in an understanding of the principles associated with distillation. First, because the reaction is occurring concurrently with distillation, the initial reaction products are removed from the reaction zone as quickly as possible. Second, because all the components are boiling, the temperature of reaction is controlled by the boiling point of the mixture at the system pressure. The heat of reaction simply creates more boil up but no increase in temperature. Third, the reaction has an increased driving force because the reaction products have been removed and cannot contribute to a reverse reaction (LeChatelier's Principle).

As a result, a great deal of control over the rate of reaction and distribution of products can be achieved by regulating the system pressure. Also, adjusting the throughput (residence time=liquid hourly space velocity$^{-1}$) gives further control of product distribution and degree of butene-1 to butene-2 conversion.

The temperature in the distillation column reactor is determined by the boiling point of the liquid mixture present at any given pressure. The temperature in the lower portions of the column will reflect the constitution of the material in that part of the column which will be higher than the overhead; that is, at constant pressure a change in the temperature of the system indicates a change in the composition in the column. To change the temperature the pressure is changed. Temperature control in the reaction zone is thus effected by a change in pressure; by increasing the pressure, the temperature in the system is increased, and vice versa.

The distillation column reactor is generally operated at overhead temperatures in the range of 80 to 180° F., more preferably 100 to 150° F. at pressures in the range of 50 to 110 psig (bearing in mind the effect of pressure on temperature as discussed above). In its more preferred embodiments the present process is operated under conditions, particularly temperature and pressure, which tend to exclude butene-2 from contact with the catalyst while holding the butene-1 in contact with it. Thus, as butene-1 is isomerized to butene-2 it drops down in the column away from the catalyst and is removed as bottoms.

A reflux is preferably included in the system. The reflux ratio could vary over the rate 0.5:1 to 33:1. In practice, the higher ratio may be used to compensate for a short catalyst bed such as required for experimental work. In commercial size units the catalyst bed would be provided so that lower reflux and hence higher unit productivity could be obtained at lower operating cost.

It has been calculated that to obtain the same unit productivity and isobutene purity from a given feed in a conventional distillation as obtainable in the present process would impossible.

A catalyst suitable for the present process is 0.5% PdO on ⅛" Al$_2$O$_3$ (alumina) extrudates, hydroisomerization catalyst, supplied by Engelhard Industries. The catalyst is believed to be the hydride of palladium which is produced during operation. The hydrogen rate to the distillation column reactor must be sufficient to maintain the catalyst in the active form because hydrogen is lost from the catalyst by hydrogenation, especially when butadiene is contained in the feed. The hydrogen rate must be adjusted such that there is sufficient hydrogen to support the butadiene hydrogenation reaction and replace hydrogen lost from the catalyst but kept below that required for hydrogenation of butenes or to cause flooding of the column which is understood to be the "effectuating amount of hydrogen" as that term is used herein. Generally the mole ratio of hydrogen to C$_4$ hydrocarbon fed to the bed of the present invention will be about 0.01 to 0.60, preferably 0.01 to 0.10.

The hydrocarbon stream is selected as one which is high in C$_4$'s, especially normal butenes and isobutene. Saturated C$_4$'s only contribute to the vapor loading in the column. High concentrations of butadiene are not necessarily desired since it has been found that the isomerization reaction does not proceed until near completion of the butadiene hydrogenation reaction. A practical limit to butadiene is thus established by the distillation column reactor bed size and reaction time available for the hydrogenation and isomerization reactions. Additionally the butadiene can be extracted to practical limits before feeding due to its economic value. A typical candidate stream is the mixed C$_4$ stream from a fluid catalytic cracking unit (FCCU).

The FIGURE is a schematic representation of a general process to separate normal butenes from isobutene by isomerization of butene-1 while concentrating the butene-2 and isobutene in separate streams. The initial step is feeding a mixed $C_4$ stream, as from a butadiene extraction plant, to a distillation column 10. In the distillation column a mixed $C_4$ stream containing butene-1, isobutene and isobutane is removed as overheads via flow line 103 while butene-2 and normal butane are removed as bottoms via flow line 102.

The overheads are fed to distillation column reactor 40 near the bottom of a catalytic distillation section 41 which contains the supported PdO catalyst in the form of the catalytic distillation structure. Hydrogen is fed via flow line 107.

As the reactant feed contacts the catalyst any butadiene in the feed is hydrogenated to butenes and equilibrium amounts of butene-1 and butene-2 are produced at the catalyst. The butene-2 is immediately distilled away and taken as bottoms driving the reaction at the catalyst sites toward the production of butene-2.

Stripping section 42 of the column contains a conventional distillation structure such as bubble cap, sieve trays or inert packing to allow for complete separation of the butene-2 product from the lower boiling isobutene and isobutane. Any normal butane will also be removed as bottoms. The bottoms containing only butene-2 and normal butane are fed back to the distillation column 10 as reflux and eventually removed as bottoms via flow line 102.

Overhead stream 111, comprising isobutene and isobutane is condensed in condenser 50. The condensed overheads are collected in receiver separator 60 wherein the liquid isobutene and isobutane are separated from hydrogen and light materials which are vented via flow line 112. The hydrogen may be recycled to the distillation column reactor if desired (not shown). A portion of the condensed overhead product is recycled via flow line 114 to the distillation column reactor 40 as reflux. The isobutene and isobutane are removed as overheads product via flow line 113. This stream may be passed on to a splitter (not shown) for separation of the isobutene from the isobutane.

The isomerization reaction proceeds at a rate of approximately 100 times faster than hydrogenation of the butenes, so the removal of the reactants from the reaction zones prevents loss of butenes. The hydrogen rate necessary for hydrogenation of butadiene is greater than that necessary for isomerization activity but less than that which would cause flooding in the tower. Unused hydrogen may be withdrawn from condenser 50 via flow line 112 and recycled as necessary.

It should be appreciated that although the FIGURE refers to two columns, the two columns are effectively one column since all of the overheads from the first column go to the second column and all of the bottoms from the second column go back to the first column.

EXAMPLE

In the example a four-inch diameter 50 foot tower and a 3 inch 50 foot tower were coupled to simulate a tower (corresponding to column 40). The tower was packed with 20.8 pounds of 0.5 wt % PdO on alumina catalyst in structures as described in U.S. Pat. No. 5,730,843. The catalyst was divided into four equally spaced beds each ten feet in height. The remainder of the column was packed with ⅝" pall rings. The feed to the distillation column reactor was prefractionated to simulate the overheads from the distillation column 10 of the FIGURE. Conditions, flow rates and stream compositions are given in TABLE I below. Notably the overheads from the distillation column reactor contained only 0.003 wt % butene-1, 0.078 wt % normal butane and 0.004 wt % trans-butene-2. Thus a relatively butene free overheads stream was produced. The butene-1 conversion was 18% and normal butene saturation was negligible (0.175 wt %).

TABLE I

| Hours on Stream | 745 | | |
|---|---|---|---|
| Reflux Ratio | 9.4 | | |
| OH Pressure | 75 psig | | |
| Hydrogen rate | 3 scfh | | |
| | Feed 140 lbs/hr | OVHDS | BTMS |
| Rate, lbs.hr | 140 | 13.5 | 125.5 |
| Composition wt % | | | |
| isobutene | 53.5 | 79.874 | 50.463 |
| isobutane | 7.4 | 20.045 | 5.866 |
| normal butane | 18.4 | 0.078 | 20.712 |
| butene-1 | 4.7 | 0.003 | 4.507 |
| cis butene-2 | 5.2 | 0.000 | 6.214 |
| trans butene-2 | 10.5 | 0.004 | 12.238 |
| other | 0.3 | — | — |
| | 100.0 | 100.000 | 100.000 |

Butene-1 conversion 18 percent
normal butene saturation 0.05 lbs/hr

The invention claimed is:

1. A process for the separation of normal butenes from isobutene contained in a mixed $C_4$ stream comprising the steps of:
    (a) feeding (1) a mixed $C_4$ stream containing butene-1, butene-2, and isobutene and (2) hydrogen to a distillation column reactor containing a bed of alumina supported PdO catalyst;
    (b) concurrently in said distillation column reactor
        (i) contacting said butene-1 and said hydrogen with said bed to isomrize said butene-1 to butene-2 and
        (ii) separating said butene-2 from said isobutene by fractional distillation in said bed;
    (c) removing isobutene containing proportionally less butene-1 than contained in said $C_4$ stream from said distillation column reactor as overheads; and
    (d) removing butene-2 from said distillation column reactor as bottoms.

2. The process according to claim 1 comprising fractionating a portion of said mixed $C_4$ stream in the absence of said catalyst prior to contact of said portion of $C_4$ contacting said catalyst.

3. The process according to claim 2 wherein said mixed $C_4$ stream also contains normal butane and isobutane and said normal butane is removed from said distillation column reactor along with said bottoms and said isobutane is removed from said distillation column reactor along with said overheads.

4. The process according to claim 2 wherein said distillation column reactor is operated under conditions of temperature and pressure to exclude butene-2 from contact with said catalyst and to maintain said butene-1 in contact with said catalyst.

5. The process according to claim 1 wherein said mixed $C_4$ stream contains butadiene and said butadiene is hydrogenated to butene in said bed.

6. A process for the separation of normal butenes from isobutene contained in a mixed $C_4$ stream comprising the steps of:
    (a) feeding a mixed $C_4$ stream containing butene-1, butene-2, normal butane, isobutene and isobutane to a distillation column reactor wherein said $C_4$ stream is fractionated to a lighter fraction containing butene-1, isobutene and isobutane and a heavier fraction containing butene-2 and normal butane;

(b) feeding the lighter fraction and hydrogen to a bed of alumina supported PdO catalyst prepared as a distillation structure;

(c) concurrently in said distillation column reactor
  (i) contacting said butene-1 and said hydrogen with said catalyst to isomerize said butene-1 to butene-2 and
  (ii) separating said butene-2 from said isobutene and isobutane by fractional distillation in said bed;

(d) withdrawing a bottoms from said distillation column reactor containing butene-2; and (e) withdrawing an overheads stream from said distillation column reactor containing isobutene and isobutane.

7. The process according to claim 6 wherein said process is carried out at a temperature in the range of 80 to 180° F. and a pressure in the range of 50 to 110 psig.

8. The process of claim 7 wherein said mixed $C_4$ stream contains butadiene and said butadiene is hydrogenated to butene in said bed.

9. The process according to claim 6 wherein said second overheads is fed to a splitter where said isobutene is separated from said isobutane by fractional distillation.

10. The process according to claim 7 wherein said process is carried out at a temperature in the range of 100 to 150° F.

11. The process according to claim 1 wherein said process is carried out at a reflux ratio at a rate in the range of 0.5:1 to 33:1.

12. The process according to claim 1 wherein said hydrogen is fed at an effectuating rate.

13. The process according to claim 6 wherein said hydrogen is fed at a rate to provide sufficient hydrogen to support butadiene hydrogenation reaction and replace hydrogen lost from the catalyst but kept below that required for hydrogenation of butenes or to cause flooding of the distillation column reactor.

14. The process according to claim 6 wherein said mixed $C_4$ stream is from a fluid catalytic cracking unit.

* * * * *